United States Patent [19]

Farmer, III et al.

[11] 4,288,427

[45] Sep. 8, 1981

[54] CONDITIONING SHAMPOO COMPOSITION AND INGREDIENT THEREFOR

[75] Inventors: Robert F. Farmer, III, Rockville, Md.; Phillip E. Sokol, deceased, late of Rockville, Md., by Eunice Sokol, legal representative

[73] Assignee: The Gillette Company, Boston, Mass.

[21] Appl. No.: 68,369

[22] Filed: Aug. 21, 1979

[51] Int. Cl.³ .............................................. A61K 7/06
[52] U.S. Cl. ...................................... 424/70; 525/344; 526/240; 526/287; 526/344
[58] Field of Search ................... 424/70; 526/240, 287, 526/344; 525/344

[56] References Cited

U.S. PATENT DOCUMENTS

| | | | |
|---|---|---|---|
| 2,477,383 | 7/1949 | Lewis | 252/537 |
| 2,486,921 | 11/1949 | Byerly | 252/238 X |
| 3,219,608 | 11/1965 | Ingleby et al. | 526/287 |
| 3,562,170 | 2/1971 | Zorayan et al. | 424/70 X |
| 3,577,518 | 5/1971 | Shepherd et al. | 424/71 X |
| 3,844,986 | 11/1974 | Tomatu et al. | 526/287 |
| 3,925,241 | 12/1975 | Schmolka | 424/70 |
| 3,937,802 | 2/1976 | Fujimoto et al. | 424/70 |
| 3,950,417 | 4/1976 | Verdicchio et al. | 424/70 |
| 3,962,418 | 6/1976 | Birkofer | 424/70 |
| 3,969,500 | 7/1976 | Kennerley | 424/71 X |
| 3,972,336 | 8/1976 | Nowak, Jr. et al. | 424/71 X |
| 4,003,991 | 1/1977 | Krohn et al. | 424/81 |
| 4,195,077 | 3/1980 | Marsh et al. | 424/70 |

Primary Examiner—Dale R. Ore
Attorney, Agent, or Firm—Leonard J. Janowski

[57] ABSTRACT

This invention deals with novel sulfated copolymers of hydroxyethyl methacrylate and alkyl esters of acrylic acid and sulfated copolymers of hydroxyethyl acrylate and alkyl esters of methacrylic acid. The copolymers are useful as components in aqueous hair shampoo systems to provide an after-shampoo conditioning effect.

8 Claims, No Drawings

CONDITIONING SHAMPOO COMPOSITION AND INGREDIENT THEREFOR

BACKGROUND

This invention deals with novel sulfated copolymers of hydroxyethyl methacrylate and alkyl esters of acrylic acid and sulfated copolymers of hydroxyethyl acrylate and alkyl esters of methacrylic acid. The copolymers are useful as components in aqueous hair shampoo systems to provide an after-shampoo conditioning effect.

The primary function of any hair shampoo product is, of course, to thoroughly remove from the hair accumulated deposits of sebum, airborne particulate materials, and residues of hair treating compositions such as hair sprays or other grooming aids. At least as important, however, from the standpoint of consumer satisfaction are the wet and dry combing properties of the hair after shampooing and the feel and appearance of the hair. As a general rule, shampoos that thoroughly clean the hair tend to leave it hard to comb and in a dry, fly-away condition. Conversely, shampoos which avoid "over-drying" the hair usually do so at the expense of cleaning effectiveness.

We have discovered a class of materials which when formulated in conventional, aqueous shampoo systems, provide unexpected post-shampoo conditioning benefits. Not only is a smooth, soft feel imparted to the hair, but combing, both wet and dry, is markedly improved. Furthermore, the hair appears to have more body, being more manageable, and exhibits improved luster. These benefits are derived from the inclusion of certain sulfated copolymers of hydroxyethyl methacrylate and alkyl esters of acrylic acid and sulfated copolymers of hydroxyethyl acrylate and alkyl esters of methacrylic acid as will be hereinafter more fully described.

The prior art describes anionic shampoos containing a variety of polymeric ingredients, for example U.S. Pat. No. 3,969,500 dealing with hair shampoos containing water soluble carboxylic linear polymers such as polymethacrylic acid. The art also described hair treating compositions such as hair sprays and setting agents based upon a variety of acrylic and sulfonated polymers, for example U.S. Pat. Nos. 3,577,518 and 3,972,336 dealing with hair setting preparations based upon acrylic or methacrylic esters and sulfonated polystyrene respectively. Nowhere, however, does the art teach that sulfated copolymers of hydroxyethyl methacrylate and alkyl esters of acrylic acid and sulfated copolymers of hydroxyethyl acrylate and alkyl esters of methacrylic acid may be useful as surfactant conditioning ingredients in aqueous hair shampoo compositions.

SUMMARY OF THE INVENTION

We have discovered a new group of compounds useful as components in aqueous human hair shampoo compositions comprising sulfated copolymers of hydroxyethyl methacrylate and alkyl esters of acrylic acid and sulfated copolymers of hydroxyethyl acrylate and alkyl esters of methacrylic acid having the formula:

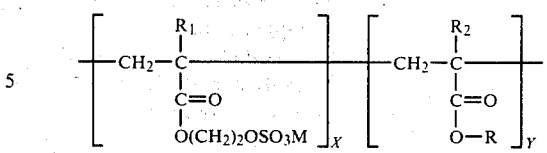

in which the molar ratio of X to Y is from 3:1 to 1:2, in which R is a straight or branched chain alkyl group having 4–18 carbon atoms, in which $R_1$ is $-CH_3$ when $R_2$ is $-H$, in which $R_1$ is $-H$ when $R_2$ is $-CH_3$, in which the ratio of carbon atoms to $-OSO_3M$ groups is from 1:8 to 1:16, preferably from 1:11 to 1:14, in which M is sodium, potassium, or triethanolamine. The molecular weight range of the useful polymers is from about 5,000 to 500,000 with a preferred molecular weight range of 15,000 to 200,000.

DETAILED DESCRIPTION OF THE INVENTION

Hydroxyethyl acrylate and methacrylate and alkyl acrylates and methacrylates are monomers which are presently commercially available in bulk quantities at low cost. We have found that when these materials are combined in a copolymer as described herein, the backbone possesses randomly spaced pendant methyl and ester groups to yield a material having film properties intermediate between the rubbery all-acrylates and the more brittle all-methacrylate analogues. We have solution copolymerized a variety of n-alkyl acrylates or methacrylates having alkyl chain lengths of $C_4$ to $C_{18}$ with hydroxyethyl methacrylate or acrylate over a variety of comonomer ratios using the following general preparation.

To a three-neck flask equipped with a stirrer, thermometer and reflux condenser is added a dioxane solution of the comonomers at a total solids concentration of about 25%. Benzoyl peroxide at a concentration of 2% of the monomer solids is then added and dissolved. Heat is applied gradually. As 80° C. is approached, an exotherm occurs which brings the solution to reflux. Reflux is then maintained for six hours. The extent of polymerization is determined by measuring the % solids of the reaction mixture. If a solids concentration of 25% is not reached, additional benzoyl peroxide (about 10% of the original amount) is added and reflux is continued until complete polymerization is obtained. Copolymers prepared in this way typically exhibit molecular weights of approximately 30,000.

Partial or complete sulfation of the hydroxyl groups present in the polymers produced above is accomplished by the slow addition of an equivalent of chlorosulfonic acid to a dioxane-methylene chloride solution of the polymeric material. The stirred reaction solution is cooled to prevent the temperature from exceeding 25° C. Upon completion of the addition, the solution is sparged with nitrogen to remove any HCl which is present. The sulfuric acid ester is then converted to the sodium salt by pouring the reaction mixture into an equivalent amount of stirred aqueous sodium hydroxide. The pH of the resulting emulsion is adjusted to 8–9 with additional aqueous sodium hydroxide. The organic solvents are then removed by distillation to yield a concentrated aqueous solution of the sodium salt of the sulfated polymer. The ionic group of the surface active copolymers prepared as described above is the sulfate ion, the most hydrophilic of the anionic functional groups. It is especially useful in the formulation of compositions for the treatment of hair and skin because of its minimal tendencies to complex with metal ions and its minimal sensitivity to hard water.

In the formulation of copolymers described above, in aqueous shampoo compositions, conventional formulation techniques may be employed. Any anionic, nonionic or amphoteric surface active agent known to be useful in the formulation of hair shampoo compositions may be likewise used in the compositions of this invention. Among the various species which may be combined with the copolymers described herein to yield conditioning shampoo compositions are the following:

Anionics $C_{10}$ to $C_{18}$ alkyl sarcosines.

Alcohol sulfates including the $NH_4$, Mg, Na, K, triethanolamine, diethanolamine, and monoethanolamine salts of monoalcohols having 10 to 18 carbon atoms and their ethoxylated derivatives having 1 to 200 moles of ethoxylation.

Alkylaryl sulfonates including the $NH_4$, Ca, Na, K, triethanolamine and isopropanolamine salts where the aryl group is selected from the group consisting of benzene, cumene, toluene, xylene and the alkyl group has 1 to 13 carbon atoms.

$C_{10}$ to $C_{18}$ alkyl amine and amide sulfonates.

Benzene, cumene, toluene and xylene sulfonates.

Ethoxylated alkylphenols having alkyl groups of 8 to 12 carbon atoms and having 4 to 200 moles of ethoxylation.

Diphenyl sulfonates including dibutylphenylphenol sodium disulfonate and $C_{10}$ to $C_{12}$ diphenylether disulfonates.

Fatty acid soaps comprising the Li, Na, K. $NH_4$, monoethanolamine, diethanolamine, triethanolamine and isopropanolamine salts of fatty acids having 10 to 24 carbon atoms.

Sulfated and sulfonated esters including those having the structure $R_1CO_3R_2$ where $R_1$=an alkyl group having 9 to 17 carbon atoms, $R_2$ is an alkyl group having 1 to 3 carbon atoms.

Sulfated and sulfonated oils from the group consisting of olive, soybean, peanut, tallow, castor, hydrogenated castor, sperm, linseed, safflower, neatsfoot and coconut oils.

Sulfated and sulfonated oils containing fatty acids having 10 to 18 carbon atoms.

Olefin sulfates and sulfonates having 10 to 18 carbon atoms.

Petroleum sulfonates having 10 to 18 carbon atoms.

Ether sulfates including the $NH_4$, Na, K, triethanolamine, diethanolamine and monoethanolamine salts of compounds having alkyl groups with from 10 to 18 carbons.

Sulfosuccinates including the sodium, monoethanolamine and isopropanolamine salts of straight chain or branched derivatives having 4 to 18 carbon atoms.

Taurates including the sodium salts of taurates having 10 to 18 carbon atoms, N-methyltaurates having 10 to 18 carbon atoms and N-cyclohexyltaurates having 10 to 18 carbon atoms.

Amide sulfates having 10 to 18 carbon atoms.

Nonionics

Ethoxylated mono and polyhydric alcohols having 10 to 18 carbon atoms and more than 5 moles of ethoxylation.

Ethoxylated alkylphenols having 6 to 12 carbon atoms in the alkyl group and 5 to 200 moles of ethoxylation.

Ethoxylated fatty acids having 10 to 18 carbon atoms and 5 to 200 moles of ethoxylation.

Fatty alkanolamides having the structure $R_1CONR_2R_3$ where $R_1=C_5-C_{17}$ and $R_2=R_3=CH_3$
or $R_1=C_5-C_{17}$, $R_2=H$, and $R_3=CH_2CH_2OH$ or $CH_2CHOHCH_3$
or $R_1=C_5-C_{17}$, $R_2=R_3=CH_2CH_2OH$
and their ethoxylated derivatives having 5 to 200 moles of ethoxylation.

Ethoxylated lanolin derivatives.

Ethoxylated sorbitans, including fatty acid esters of sorbitol having 10 to 18 carbon atoms and ethoxylated with 10 to 200 moles of ethylene oxide.

Amphoteric

Imidazoline derivatives having the following structures:

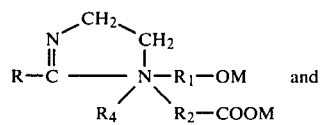
and
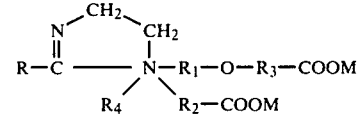

in which R is a hydrocarbon group having from 4 to 18 carbon atoms.

$R_1$, $R_2$ and $R_3$ are selected from the group consisting of
(a) aliphatic hydrocarbon groups of 1 to 4 carbon atoms,
(b) hydroxy-substituted aliphatic hydrocarbon groups of 1 to 4 carbon atoms,
(c) aliphatic hydrocarbon groups having a single ether linkage and of 2 to 4 carbon atoms,
(d) hydroxy-substituted aliphatic hydrocarbon groups having single ether linkage and of 2 to 4 carbon atoms,
(e) aliphatic keto groups containing only a single keto linkage and otherwise being hydrocarbon of 2 to 4 carbon atoms,
(f) aliphatic keto groups containing only a single keto linkage and otherwise being hydroxy-substituted hydrocarbon of 2 to 4 carbon atoms.

$R_4$ is selected from the group consisting of
(a) a hydroxyl group and
(b) the group $-OSO_3(CH_2CH_2O)_nR_5$ in which $R_5$ is a hydrocarbon group containing 8 to 18 carbon atoms and n is a whole number from 0 to 4 inclusive, and M is an alkali metal.

Betaines having the structure $R_1R_2R_3N^{30}CH_2CO_2^-$ where
$R_1$ and $R_2$ are methyl groups, $R_3$ is an alkyl group having 10 to 18 carbon atoms.

We have found that the percentage of primary surface active agent to employed may range from 5 to 25 with 8 to 20 being preferred and that of the conditioning copolymer may range from 1 to 10 with 3 to 7 being preferred.

Other conventional shampoo additives such as foam boosters, opacifiers, perfumes, and the like may be added as is well known to those skilled in the art. Particular care should be taken in selecting a thickener which is chemically compatible with the conditioning copolymer ingredient. We have found hydroxyethyl cellulose to be suitable.

EXAMPLE I

Preparation of Sulfated Copolymer of Hydroxyethyl Methacrylate and n-Butyl Acrylate (I)

a. Synthesis of Hydroxyethyl Methacrylate (HEMA)-n-Butyl Acrylate (BA) Copolymer (Ia)

To a three-neck flask equipped with stirrer, thermometer and reflux condenser were added 130 g (1.00 mole) HEMA, 128 g (1.00 mole) BA and 775 g anhydrous dioxane. Benzoyl peroxide initiator (5.2 g, 2% by weight of the monomers) was then added and dissolved. Heat was applied gradually. As 80° C. was approached, an exotherm occurred which brought the solution to reflux. Reflux was maintained for a minimum of six hours. The extent of the polymerization was determined by measuring the % solids of the reaction mixture. If a solids concentration of 25% was not achieved, additional benzoyl peroxide (10% of the original amount) was added, and refluxing continued until complete polymerization was obtained.

b. Sulfation of Hydroxyethyl Methacrylate-n-Butyl Acrylate Copolymer

To a three-neck flask equipped with stirrer, thermometer, dropping funnel and reflux condenser was added 1032 g of dioxane solution of compound Ia. Anhydrous methylene chloride (688 g) was added to lower the solids content to 15%. Chlorosulfonic acid (122 g, 1.05 moles) was added to the dropping funnel. The acid was slowly added to the stirred solution, and cooling was applied to maintain a solution temperature less than 25° C. Upon completion of the addition, the solution was sparged with nitrogen to remove dissolved HCl. The sulfuric acid ester solution of Ia was then added to 40 g sodium hydroxide dissolved in 2 L of water. Additional 10% aqueous sodium hydroxide was added to stabilize the pH at 8–9. The organic solvents were then removed by distillation to yield an aqueous solution of compound I.

EXAMPLE II

Preparation of Sulfated Copolymer of Hydroxyethyl Methacrylate and n-Octyl Acrylate (II)

a. Synthesis of Hydroxyethyl Methacrylate (HEMA)-n-Octyl Acrylate (OA) Copolymer (IIa)

Following the procedure given in Example Ia, 130 g (1.00 mole) HEMA, 134 g (0.717 mole) OA and 791 g anhydrous dioxane were added to the reaction apparatus. Benzoyl peroxide (5.3 g) was added to the flask and dissolved. Heat was applied, and the polymerization reaction taken to completion. A 25% solution of compound IIa in dioxane was obtained.

b. Sulfation of Hydroxyethyl Methacrylate-n-Octyl Acrylate Copolymer

Following the procedure given in Example Ib, 1055 g of dioxane solution of compound Ib was added to the reaction apparatus. Anhydrous methylene chloride (703 g) was added to lower the solids content to 15%. The sulfation reaction was conducted as described in Example Ib by dropwise addition of 133 g chlorosulfonic acid. After HCl removal, neutralization of the sulfuric acid ester of the copolymer was carried out by slow addition of the acid ester solution to 40 g sodium hydroxide dissolved in 2 L of water. After pH adjustment to 8–9 with additional sodium hydroxide, the organic solvents were removed by distillation to afford an aqueous solution of compound II.

EXAMPLE III

Preparation of Sulfated Copolymer of Hydroxyethyl Methacrylate and n-Octadecyl Acrylate (III)

a. Synthesis of Hydroxyethyl Methacrylate (HEMA)-n-Octadecyl Acrylate (OdA) Copolymer (IIIa)

Following the procedure given in Example Ia, 130 g (1.00 mole) HEMA, 123 g (0.381 mole) OdA and 760 g anhydrous dioxane were added to the reaction apparatus. Benzoyl peroxide (5.1 g) was added to the flask and dissolved. Heat was applied, and the polymerization reaction taken to completion. A 25% solution of compound IIIa in dioxane was obtained.

b. Sulfation of Hydroxyethyl Methacrylate-n-Octadecyl Acrylate Copolymer

Following the procedure given in Example Ib, 1014 g of dioxane solution of compound IIIa was added to the reaction apparatus. Anhydrous methylene chloride (676 g) was added to lower the solids contenents to 15%. The sulfation reaction was conducted as described in Example Ib by dropwise addition of 122 g chlorosulfonic acid. After HCl removal, neutralization of the sulfuric acid ester of the copolymer was carried out by slow addition of the acid ester solution to 40 g sodium hydroxide dissolved in 2 L of water. After pH adjustment to 8–9 with additional sodium hydroxide, the organic solvent were removed by distillation to afford an aqueous solution of compound III.

EXAMPLE IV

Preparation of Sulfated Copolymer of Hydroxyethyl Acrylate and n-Hexyl Methacrylate (IV)

a. Synthesis of Hydroxyethyl Acrylate (HEA)-n-Hexyl Methacrylate (HMA) Copolymer (IVa)

Following the procedure given in Example Ia, 116 g HEA, 123 g HMA and 760 g anhydrous dioxane were added to the reaction apparatus. Benzoyl peroxide (5.1 g) was added to the flask and dissolved. Heat was applied, and the polymerization reaction taken to completion. A 25% solution of compound IVa in dioxane was obtained.

b. Sulfation of Hydroxyethyl Acrylate-n-Hexyl Methacrylate Copolymer

Following the procedure given in Example Ib, 1014 g of dioxane solution of compound IVb was added to the reaction apparatus. Anhydrous methylene chloride (676 g) was added to lower the solids content to 15%. The sulfation reaction was conducted as described in Example Ib by dropwise addition of 122 g chlorosulfonic acid. After HCl removal, neutralization of the sulfuric acid ester of the copolymer was carried out by slow addition of the acid ester solution to 40 g sodium hydroxide dissolved in 2 L of water. After pH adjustment to 8 to 9 with additional sodium hydroxide, the organic solvents were removed to afford an aqueous solution of compound IV.

EXAMPLE V

The following shampoo composition was prepared.

| Ingredient | % by Weight |
| --- | --- |
| Hydroxyethyl cellulose | 0.5 |
| Triethanolamine lauryl sulfate | 5.5 |
| Lauric diethanolamide | 3.3 |
| Sulfated copolymer of hydroxyethyl methacrylate and n-octyl acrylate | 5.5 |
| Perfume, preservative, and dye | 0.6 |
| Water | q.s. to 100 |

The composition was prepared by first dispersing the hydroxyethyl cellulose in water at 65° C. and stirring until hydration was complete. Then with continued stirring, the other ingredients were added and the compositions cooled with stirring to yield a transparent shampoo composition. Evaluation of the composition by a panel of 23 subjects showed that the majority of users rated the test composition to be as good or better than their normal system (either shampoo alone or shampoo combined with post-shampoo conditioning rinse) for the properties of lather, rinsability, cleansing, appearance, feel, and ease of combing, both wet and dry.

EXAMPLE VI

| Ingredient | % by Weight |
| --- | --- |
| Hydroxyethyl cellulose | 0.5 |
| Coconut imidazolinium imidazolinium dicarboxylate | 7.8 |
| Sodium laurimidodipropionate | 3.0 |
| Sulfated copolymer or hydroxyethyl methacrylate and n-butyl acrylate | 6.0 |
| Perfume, preservative, color and water | q.s. to 100 |

EXAMPLE VII

| Ingredient | % by Weight |
| --- | --- |
| Hydroxyethyl cellulose | 0.5 |
| Sodium lauryl ether sulfate | 10.0 |
| Cocoamidopropylbetaine | 5.0 |
| Sulfated copolymer of hydroxyethyl acrylate and n-hexyl methacrylate | 5.0 |
| Perfume, preservative, color and water | q.s. to 100 |

EXAMPLE VIII

| Ingredient | % by Weight |
| --- | --- |
| Hydroxyethyl cellulose | 0.5 |
| Ammonium lauryl sulfate | 6.0 |
| Sulfosuccinate, coco half-ester | 2.5 |
| Lauric diethanolamide | 3.0 |
| Sulfated copolymer of hydroxethyl methacrylate and n-octadecyl acrylate | 7.0 |
| Perfume, preservative, color and water | q.s. to 100 |

Each of the above examples, when employed as a hair shampoo, provides the hair with improved combing, a smooth, soft feel, improved luster and good manageability.

Having thus disclosed the invention, what is claimed is:

1. A shampoo composition comprising an aqueous solution containing 1 to 10% by weight of a compound having the formula

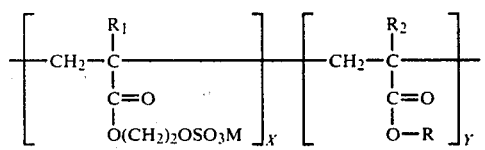

In which the molar ratio of X to Y is from 3:1 to 1:2, in which R is a straight or branched chain alkyl group having 4–18 carbon atoms, in which $R_1$ is $-CH_3$ when $R_2$ is $-H$, in which $R_1$ is $-H$ when $R_2$ is $-CH_3$, in which the ratio of carbon atoms to $-OSO_3M$ groups is from 1:8 to 1:16, and in which M is sodium, potassium or triethanolamine, in combination with 5–25% by weight of a surface active agent selected from the class consisting of anionic, nonionic, and ampholytic surface active agents.

2. The composition as described in claim 1 in which the molecular weight of said compound is from 5,000 to 500,000.

3. The composition as described in claim 1 containing 3–7% of the compound and 8–20% of the surface active agent.

4. The composition as described in claim 1 in which the ratio of carbon atoms to $-OSO_3M$ groups is from 1:11 to 1:14.

5. The composition as described in claim 3 containing 3–7% of the compound, 8–20% of the surface active agent, in which the ratio of carbon atoms to $-OSO_3M$ groups is from 1:11 to 1:14 and containing hydroxyethyl cellulose as a thickener.

6. A compound of the formula

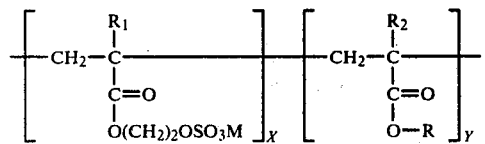

in which the molar ratio of X to Y is from 3:1 to 1:2, in which R is a straight or branched chain alkyl group having 4 to 18 carbon atoms, in which $R_1$ is $-CH_3$ when $R_2$ is $-H$, in which $R_1$ is $-H$ when $R_2$ is $-CH_3$, in which the ratio of carbon atoms to $-OSO_3M$ groups is from 1:8 to 1:16, and in which M is sodium, potassium, or triethanolamine.

7. A compound as described in claim 6 having a molecular weight of 5,000 to 500,000.

8. A compound as described in claim 6 in which the ratio of carbon atoms to $-OSO_3M$ groups is from 1:11 to 1:14 and having a molecular weight of 15,000 to 200,000.

* * * * *